(12) United States Patent
Chen et al.

(10) Patent No.: US 11,903,591 B2
(45) Date of Patent: Feb. 20, 2024

(54) SURGICAL POWER DRILL SYSTEM

(71) Applicant: POINT ROBOTICS (SINGAPORE) PTE. LTD., Singapore (SG)

(72) Inventors: Chih-Wei Chen, Hsinchu (TW); Hao-Kai Chou, Hsinchu (TW); Xiu-Yun Xiao, Hsinchu (TW)

(73) Assignee: POINT ROBOTICS (SINGAPORE) PTE. LTD., Singapore (SG)

( * ) Notice: Subject to any disclaimer, the term of this patent is extended or adjusted under 35 U.S.C. 154(b) by 330 days.

(21) Appl. No.: 17/317,924

(22) Filed: May 12, 2021

(65) Prior Publication Data
US 2022/0361897 A1 Nov. 17, 2022

(51) Int. Cl.
*A61B 17/16* (2006.01)
*A61B 90/00* (2016.01)
*A61B 17/00* (2006.01)

(52) U.S. Cl.
CPC ...... *A61B 17/1624* (2013.01); *A61B 17/1631* (2013.01); *A61B 90/39* (2016.02); *A61B 2017/00367* (2013.01); *A61B 2017/00876* (2013.01); *A61B 2090/3975* (2016.02)

(58) Field of Classification Search
CPC ............ A61B 17/1624; A61B 17/1626; A61B 17/1628; A61B 17/1633
See application file for complete search history.

(56) References Cited

U.S. PATENT DOCUMENTS

| 10,245,043 | B2* | 4/2019 | Xie | A61B 17/1633 |
| 10,695,074 | B2* | 6/2020 | Carusillo | A61B 90/03 |
| 2009/0326537 | A1* | 12/2009 | Anderson | A61B 17/17 606/80 |
| 2015/0078849 | A1* | 3/2015 | Lo | A61B 17/1624 408/124 |
| 2016/0206328 | A1* | 7/2016 | Lo | A61B 17/1626 |
| 2020/0330116 | A1* | 10/2020 | Bornhoft | A61B 17/1624 |
| 2020/0367989 | A1* | 11/2020 | Bono | A61B 17/16 |
| 2023/0293189 | A1* | 9/2023 | Delman | A61B 17/1624 606/80 |

* cited by examiner

*Primary Examiner* — Matthew J Lawson
(74) *Attorney, Agent, or Firm* — Li & Cai Intellectual Property Office

(57) ABSTRACT

A surgical power drill system includes a housing unit, a driving unit, a tool holder, and a screw member. The driving unit is movably mounted in the housing unit and includes a motor and a motor shaft coupled to the motor. The driving unit is movable relative to the housing unit between a distal position, where the driving unit is distal from a front end of the housing unit, and a proximate position, where the driving unit is proximate to the front end of the housing unit. The tool holder is coupled to a first end portion of the motor shaft. The screw member is coupled to a second end portion of the motor shaft.

17 Claims, 17 Drawing Sheets

SURGICAL POWER DRILL SYSTEM

BACKGROUND

A conventional surgical drill includes a drill housing, a driving unit in the drill housing, and a tool holder connected to a motor shaft of the driving unit. When it is desired to make a hole in a bone of a patient, a shank of a tool bit is fixed into the tool holder. Then, a tip of the tool bit is aligned with and pressed against a location on the bone. Next, a motor of the driving unit is turned on, resulting in rotation of the motor shaft and co-rotation of the tool holder as well as the tool bit, whereby a hole is drilled in the bone.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Detailed descriptions of the present disclosure are illustrated below in conjunction with the accompanying drawings. However, it is to be understood that the descriptions and the accompanying drawings disclosed herein are merely illustrative and exemplary and not intended to limit the scope of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Figure 1:
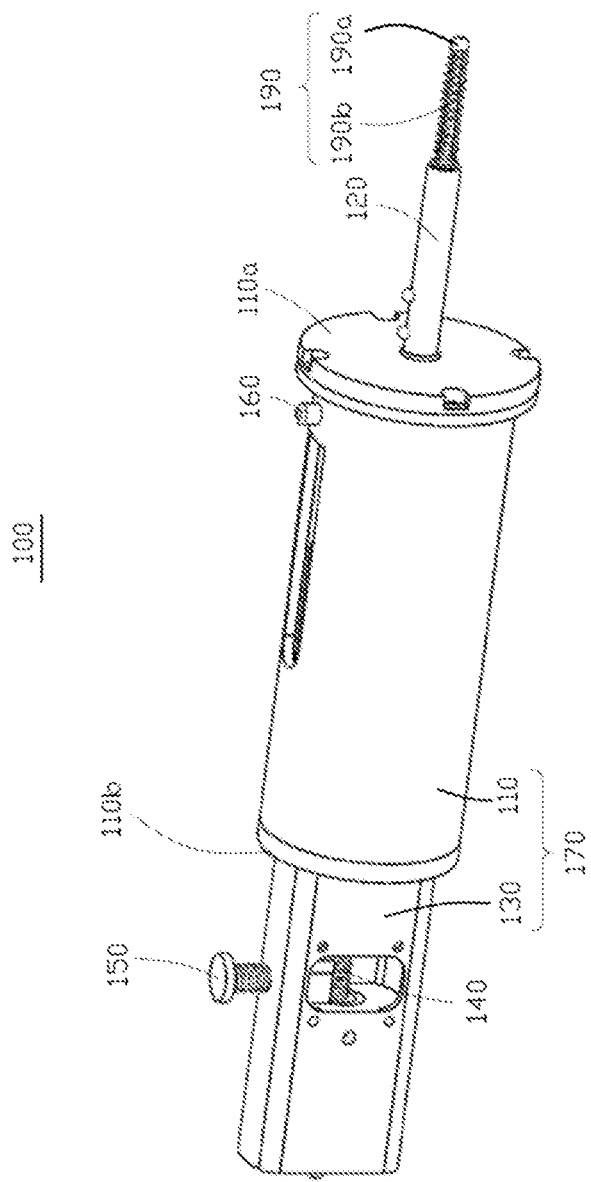
FIG. 1 is a schematic perspective view illustrating a surgical power drill system according to the first exemplary embodiment of the present disclosure.

FIG. 1 is a schematic perspective view illustrating a surgical power drill system 100 according to the first exemplary embodiment of the present disclosure. The surgical power drill system 100 is suitable for use in surgical grinding/drilling procedures, e.g., orthopedic and plastic surgery procedures, or in any non-surgical grinding/drilling procedures. As illustrated in FIG. 1, the surgical power drill system 100 includes a drill housing 110, a tool holder 120, a housing extension 130, a screw member 140, an engaging member 150, and an on/off switch 160. The drill housing 110 and the extension housing 130 constitute a housing unit 170. The drill housing 110 accommodates therein a driving unit, e.g., driving unit 200 of FIG. 2. In this exemplary embodiment, the drill housing 110 is generally cylindrical. In an alternative embodiment, the drill housing 110 has a polygonal cross-section, such as rectangular.

The drill housing 110 includes a front end 110a and a rear end 110b opposite to the front end 110a. In this exemplary embodiment, the front and rear ends 110a, 110b are fixedly mounted on the opposite ends of the drill housing 110, respectively, such as by welding. In some embodiments, the front and rear ends 110a, 110b are integral with the drill housing 110. In other embodiments, the front and rear ends 110a, 110b are detachably mounted on the opposite ends of the drill housing 110, respectively, such as by a snap engagement.

In this exemplary embodiment, the tool holder 120, e.g., a drill chuck, is connected to the driving unit 200, extends from the inside of the drill housing 110 through the front end 110a of the drill housing 110, and is configured to hold a tool bit 190, e.g., a burr screw. The tool bit 190 includes a grinding portion 190a that is at a tip thereof and that is suitable for grinding an object and an elongate drilling portion 190b that extends from the grinding portion 190a and that is suitable for drilling a hole in an object, such as a bone of a patient.

The housing extension 130 is connected detachably to the rear end 110b of the drill housing 110 and accommodates therein the screw member 140, e.g., a lead screw, a ball screw, or the like. In certain embodiments, the housing extension 130 is integral with the drill housing 110.

Figure 2:
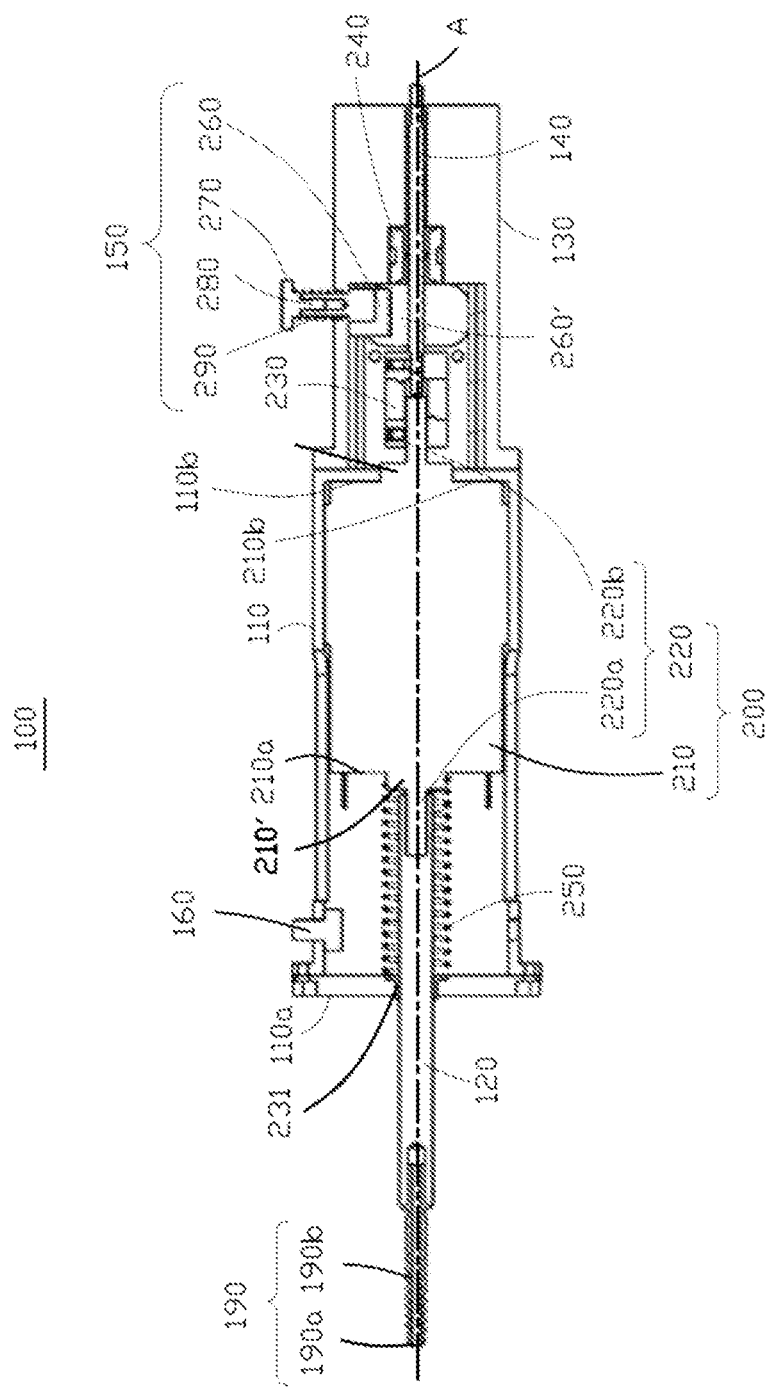
FIG. 2 is a schematic cross-sectional view illustrating a state where a driving unit of the surgical power drill system of FIG. 1 is at a distal position according to the first exemplary embodiment of the present disclosure.

The engaging member 150 is movably mounted on the housing extension 130 and includes a body member, e.g., body member 260 of FIG. 2, a head member, e.g., head member 270, a neck member, e.g., neck member 280, and a biasing member, e.g., biasing member 290. The body member 260 is disposed inside the housing extension 130 and is formed with a thread 260' at a bottom surface thereof. The head member 270 is external to the housing unit 170. The neck member 280 extends through the housing extension 130, interconnects the body member 260 and the head member 270, and has a smaller width than the body and head members 260, 270. The biasing member 290 is in the form of a spring, sleeved on the neck member 280, and has opposite ends that abut the head member 270 and the housing extension 130, respectively.

The on/off switch 160 is mounted on the drill housing 110 and is electrically connected to the driving unit 200.

Figure 3:
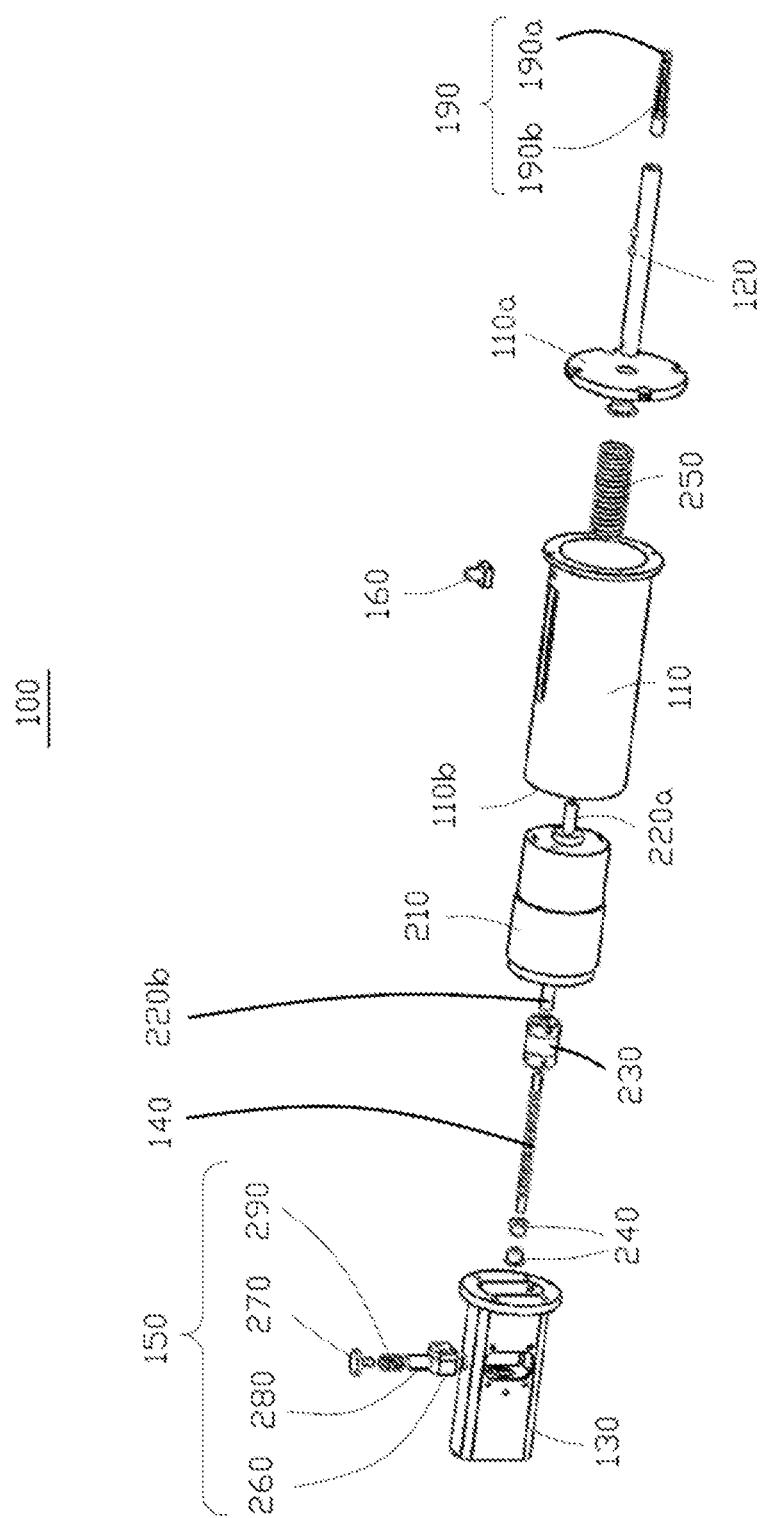
FIG. 3 is a schematic exploded view illustrating the surgical power drill system of FIG. 1 according to the first exemplary embodiment of the present disclosure.
Figure 4:
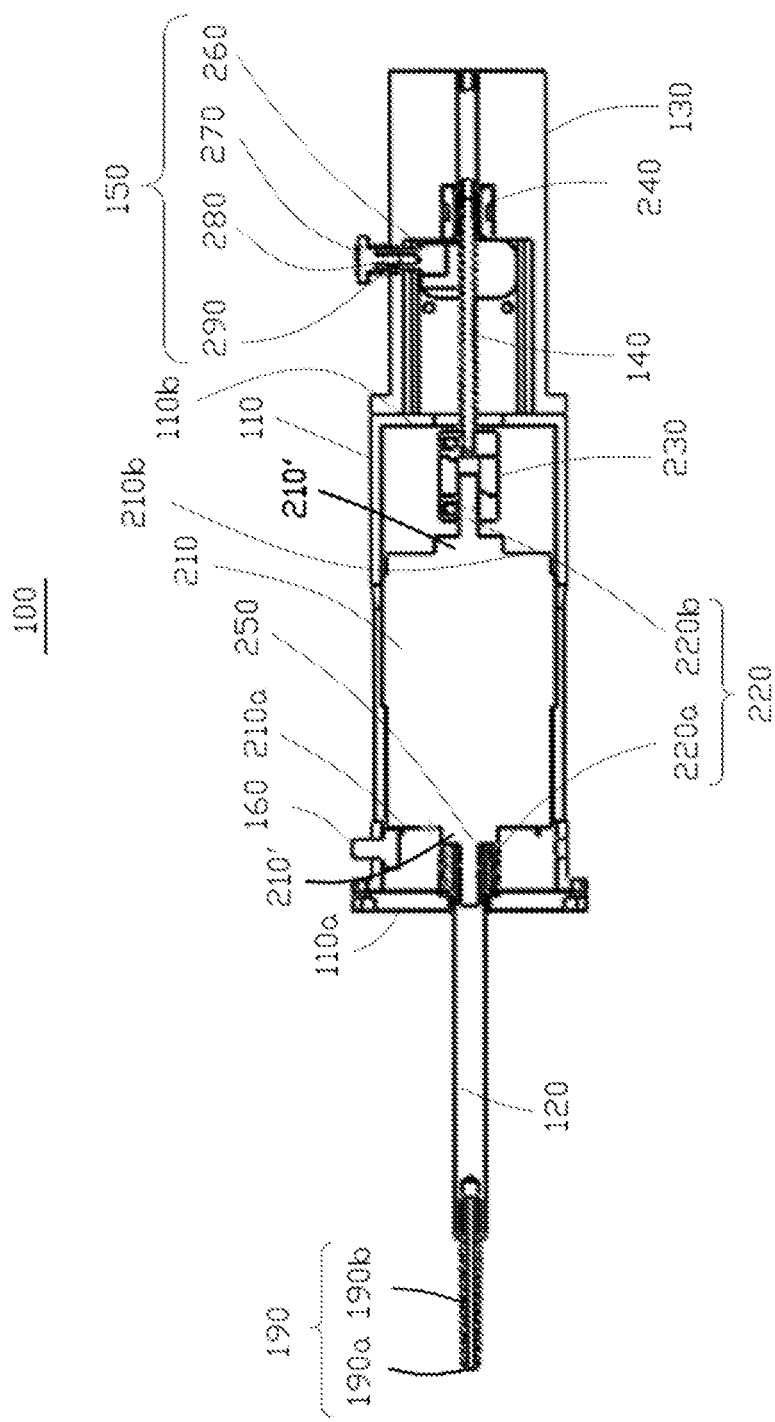
FIG. 4 is a partial schematic cross-sectional view illustrating a state where the driving unit of the surgical power drill system of FIG. 1 is at a proximate position according to the first exemplary embodiment of the present disclosure.

FIG. 2 is a schematic cross-sectional view illustrating a state where the driving unit 200 of the surgical power drill system 100 is at a distal position according to the first exemplary embodiment of the present disclosure. FIG. 3 is a schematic exploded view illustrating the surgical power drill system 100 according to the first exemplary embodiment of the present disclosure. FIG. 4 is a partial schematic cross-sectional view illustrating a state where the driving unit 200 of the surgical power drill system 100 is at a proximate position according to the first exemplary embodiment of the present disclosure. As illustrated in FIGS. 2 and 3, the surgical power drill system 100 further includes the driving unit 200, a coupler 230, a support member 240, and a biasing member 250.

Figure 7:
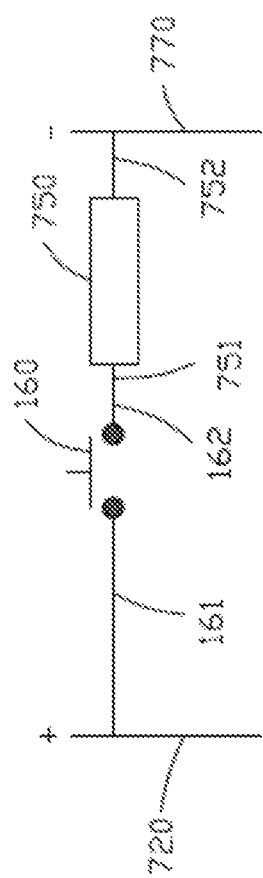
FIG. 7 is a schematic diagram illustrating an on/off switch of the surgical power drill system of FIG. 1 according to the first exemplary embodiment of the present disclosure.

The driving unit 200 is movably disposed in the drill housing 110 and includes a motor, e.g., motor 750 of FIG. 7, and a motor casing 210 that houses the motor 750. In some embodiments, the motor casing 210 may have a cross-section that corresponds to the cross-section of the drill housing 110. In other embodiments, the motor casing 210 may have a cross-section different from the cross-section of the drill housing 110.

The motor 750 includes a rotor 210' rotatably mounted on the motor casing 210 about a shaft axis (A), a stator (not shown) that is fixedly mounted on the motor casing 210 and that surrounds the rotor 210', and a motor shaft 220 connected to the rotor 210' and co-rotatable therewith about the shaft axis (A). The motor shaft 220 includes a first end portion 220a that extends from the inside of the motor casing 210 through a front end 210a of the motor casing 210 and that is connected to the tool holder 120 and a second end portion 220b that extends from the inside of the motor casing 210 through a rear end 210b of the motor casing 210 and that is connected to the screw member 140.

The coupler 230 interconnects the second end portion 220b of the motor shaft 220 and the screw member 140 such that the screw member 140 extends along the shaft axis (A) and is co-rotatable with the motor shaft 220 about the shaft axis (A). In this exemplary embodiment, the coupler 230 is sleeved on the second end portion 220b of the motor shaft 220 and the screw member 140. For example, the coupler 230 may be made from a material with a low coefficient of friction, such as plastic.

In an alternative embodiment, the motor shaft 220 is integral with the screw member 140. In other words, the motor shaft 220 and the screw member 140 are formed into one piece. In such an alternative embodiment, the surgical power drill system 100 is dispensed with the coupler 230.

It is noted herein that, when the motor 750 is turned on, the tool holder 120, the first and second end portions 220a, 220b of the motor shaft 220, and the screw member 140 rotate simultaneously.

The support member 240 is mounted in the housing extension 130, is sleeved on the screw member 140, and is configured to smoothen rotation and movement of the screw member 140 about and along the shaft axis (A). The engaging member 150 is between the coupler 230 and the support member 240. The coupler 230 is between the drill housing 110 and the support member 240.

As illustrated in FIG. 2, the surgical power drill system 100 further includes a fixing member 231 mounted on the front end 110a of the drill housing 110, sleeved on the tool holder 120, and configured to minimize friction between the tool holder 120 and the drill housing 110. Such friction causes the tool holder 120 to wear, resulting in misaligning of the first end portion 220a of the motor shaft 220, the tool holder 120, and/or the tool bit 190 with the shaft axis (A). For example, the fixing member 231 is made from a material with a low coefficient of friction, such as plastic.

In this exemplary embodiment, the driving unit 200 is movable relative to the drill housing 110 between a distal position, where the motor casing 210 is distal from the front end 110a of the drill housing 110, as illustrated in FIG. 2, and a proximate position, where the motor casing 210 is proximate to the front end 110a of the drill housing 110, as illustrated in FIG. 4.

It is noted herein that, when the driving unit 200 is at the distal position, a tip of the tool holder 120 is proximate to the front end 110a of the drill housing 110, as illustrated in FIG. 2. When the driving unit 200 is at the proximate position, the tip of the tool holder 120 is distal from the front end 110a of the drill housing 110, as shown in FIG. 4.

In addition, when the driving unit 200 is at the distal position, the coupler 230 is in the housing extension 130, as shown in FIG. 2. When the driving unit 200 is at the proximate position, the coupler 230 is in the drill housing 110, as shown in FIG. 4.

Moreover, when the driving unit 200 is at the distal position, the rear end 210b of the motor casing 210 abuts the rear end 110b of the drill housing 110, as shown in FIG. 2. When the driving unit 200 is at the proximate position, the rear end 210b of the motor casing 210 is spaced from the rear end 110b of the drill housing 110, as shown in FIG. 4.

The tool holder 120 is connected to the first end portion 220a of the motor shaft 220 such that the tool holder 120 extends along the shaft axis (A) and is co-rotatable with the motor shaft 220 about the shaft axis (A).

It is noted herein that the tool holder 120, the screw member 140, and the motor shaft 220 are tubular and in fluid communication with each other. The construction as such permits injection of a synthetic material, e.g., bone cement, by an instrument into an object, e.g., bone of a patient, through the screw member 140, the motor shaft 220, and the tool holder 120.

The biasing member 250 is configured to bias the driving unit 200 to the distal position. In this exemplary embodiment, the biasing member 250 is in the form of a spring, is sleeved on the tool holder 120 and the first end portion 220a of the motor shaft 220, and has opposite ends that abut the front end 110a of the drill housing 110 and the front end 210a of the motor casing 210, respectively. The biasing member 250 is further configured to prevent shaking of the driving unit 200 in the drill housing 110. It is noted herein that the biasing member 250 has a spring constant of k greater than or equal to a weight of the driving unit 200. The construction as such permits stable movement of the driving unit 200 between the distal and proximate positions.

It should be understood that, after reading the present disclosure, other configurations of the biasing member 250 are contemplated as being within the scope of the present disclosure so long as its intended function is achieved.

In this exemplary embodiment, the drill housing 110 or the motor casing 210 or both the drill housing 110 and the motor casing 210 is/are magnetic. For example, in some embodiments, the drill housing 110 or the motor casing 210 or both the drill housing 110 and the motor casing 210 may be a magnet. In other embodiments, the drill housing 110 or the motor casing 210 or both the drill housing 110 and the motor casing 210 may be magnetized, e.g., by an electric current or external magnetic field. The construction as such enhances prevention of the shaking of the driving unit 200 in the drill housing 110.

Figure 6:
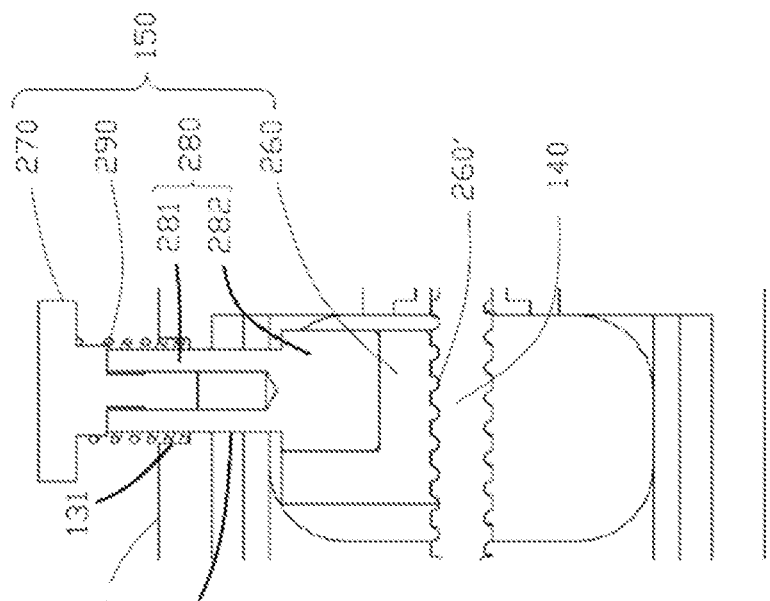
FIG. 6 is a schematic cross-sectional view illustrating a state where the engaging member of the surgical power drill system of FIG. 1 is at an engaged position according to the first exemplary embodiment of the present disclosure.
Figure 5:
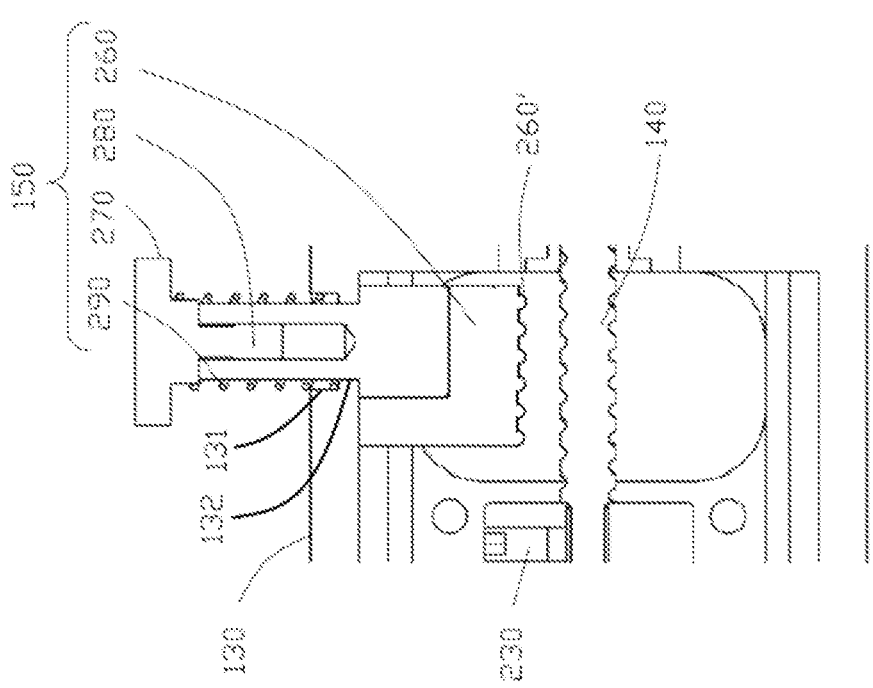
FIG. 5 is a partial schematic cross-sectional view illustrating a state where an engaging member of the surgical power drill system of FIG. 1 is at a disengaged position according to the first exemplary embodiment of the present disclosure.

FIG. 5 is a partial schematic cross-sectional view illustrating a state where the engaging member 150 of the surgical power drill system 100 is at a disengaged position according to the first exemplary embodiment of the present disclosure. FIG. 6 is a schematic cross-sectional view illustrating a state where the engaging member 150 of the surgical power drill system 100 is at an engaged position according to the first exemplary embodiment of the present disclosure. In this exemplary embodiment, the engaging member 150 is movable relative to the housing extension 130 between a disengaged position, where the thread 260' of the body member 260 disengages the screw member 140, as illustrated in FIG. 5, and an engaged position, where the thread 260' of the body member 260 engages the screw member 140, as illustrated in FIG. 6. It is noted herein that the biasing member 290 is configured to bias the engaging member 150 from the engaged position to the disengaged position.

It should be understood that, after reading the present disclosure, other configurations of the biasing member 290 are contemplated as being within the scope of the present disclosure so long as its intended function is achieved.

Although the surgical power drill system 100 of the present disclosure is exemplified with the thread 260' formed on the bottom surface of the engaging member 150, it should be understood that, after reading the present disclosure, the thread 260' may be located anywhere on the engaging member 150 so long as it engages/disengages the screw member 140 when the engaging member 150 is moved to the engaged/disengaged position.

As further illustrated in FIG. 5, the housing extension 130 is formed with first and second through holes 131, 132 that form a stepped hole. In particular, the first through hole 131 is above the second through hole 132, is in spatial communication with the second through hole 132, and has a larger diameter than the second through hole 132. The biasing member 290 is partially received in the first through hole 131.

The neck member 280 includes a first end portion 281 that extends through the first and second through holes 131, 132 and a second end portion 282 that is in the housing extension 130 and that has a larger diameter than the second through hole 132. The construction as such prevents undesired removal of the engaging member 150 from the housing extension 130.

It is noted herein that, in this exemplary embodiment, when the on/off switch 160 is switched on and the engaging member 150 is at the disengaged position, a first input voltage is applied across the motor 750 and the motor 750 has a first rotational speed, e.g., about 6000 rpm or above. When the on/off switch 160 is switched on and the engaging member 150 is at the engaged position, a second input voltage is applied across the motor 750 and the motor 750 has a second rotational speed, e.g., about 300 rpm or below, smaller than the first rotational speed.

Further, when the on/off switch 160 is switched on and the engaging member 150 is at the disengaged position, the motor 750 has a first torque, e.g., about 10 mNm or above. When the on/off switch 160 is switched on and the engaging member 150 is at the engaged position, the motor 750 has a second torque, e.g., about 100 mNm or above, larger than the first torque.

FIG. 7 is a schematic diagram illustrating the on/off switch 160 of the surgical power drill system 100 according to the first exemplary embodiment of the present disclosure. As illustrated in FIG. 7, the on/off switch 160 includes a first switch terminal 161 electrically connected to a positive terminal 720 of the surgical power drill system 100 and a second switch terminal 162 electrically connected to a first motor terminal 751 of the motor 750. The motor 750 further includes a second motor terminal 752 electrically connected to a negative terminal 770 of the surgical power drill system 100. The positive and negative terminals 720, 770 are configured to be electrically connected to positive and negative terminals of a power source, e.g., battery, respectively.

In operation, when it is desired to grind and drill a hole in an object, e.g., a bone of a patient, using the surgical power drill system 100 of the present disclosure, with further reference to FIGS. 2 and 4, a shank of a tool bit 190, e.g., a burr screw, is fixed into the tool holder 120. Then, a tip of the tool bit 190 is aligned with and pressed against a marked location on the object. Next, a switch actuator of the on/off switch 160 is depressed, thereby turning the motor 750 on. At this time, the motor shaft 220 rotates, resulting in co-rotation of the tool holder 120 as well as the tool bit 190, thereby grinding the object.

Thereafter, the engaging member 150 is moved from the disengaged position, as shown in FIG. 5, to the engaged position, as shown in FIG. 6. As a result, the driving unit 200 moves from the distal position, as shown in FIG. 2, to the proximate position, as shown in FIG. 4, whereby a hole is drilled in the object.

From the above, the surgical power drill system 100 of the present disclosure includes a motor shaft 220 connected to a screw member 140 such that each of the motor shaft 220 and the screw member 140 extends along a shaft axis (A) and an engaging member 150 that engages the screw member 140 to cause movement of a driving unit 200 in a drill housing 110. Therefore, the surgical power drill system 100 of the present disclosure has a simple structure, a compact size, and a reduced weight.

Figure 8:
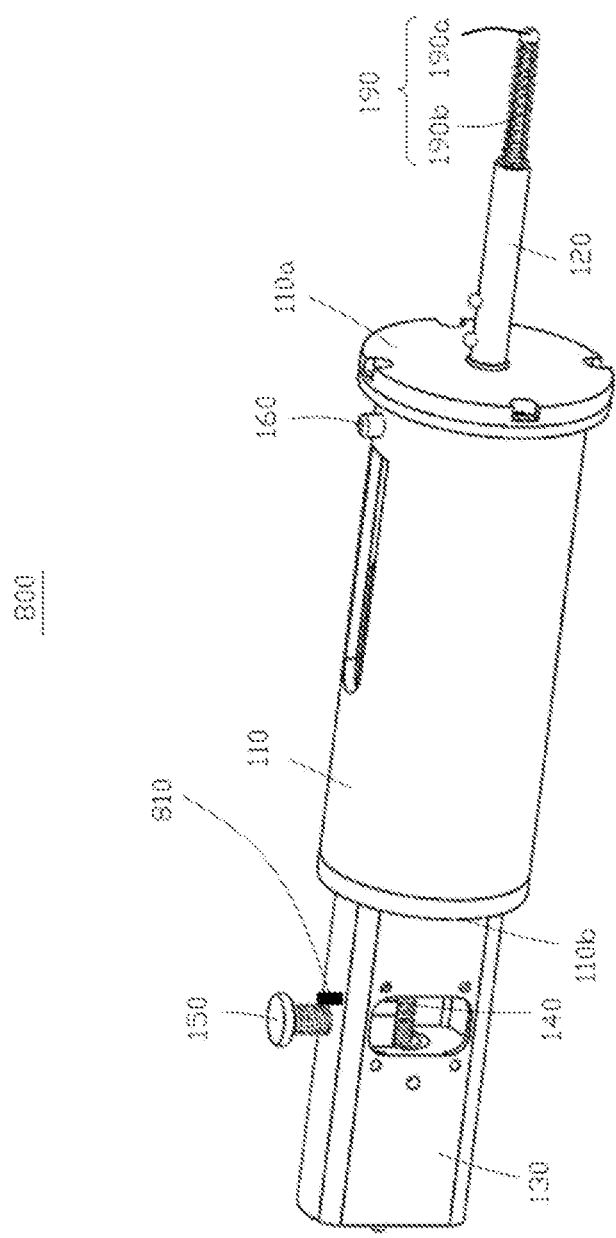
FIG. 8 is a schematic perspective view illustrating a surgical power drill system according to the second exemplary embodiment of the present disclosure.

FIG. 8 is a schematic perspective view illustrating a surgical power drill system 800 according to the second exemplary embodiment of the present disclosure. As illustrated in FIG. 8, the surgical power drill system 800 differs from the surgical power drill system 100 in that the surgical power drill system 800 further includes an engaging member switch 810 mounted on the housing extension 130 and electrically connected to a motor, e.g., motor 750, of a driving unit, e.g., driving unit 200, of the surgical power drill system 800. In this exemplary embodiment, the engaging member switch 810 includes a switch actuator that protrudes from the housing extension 130 and that is arranged adjacent the neck member, e.g., neck member 280, and under the head member, e.g., head member 270. The construction as such permits the engaging member 150 to switch the engaging member switch 810 on and off when the engaging member 150 moves between the engaged and disengaged positions, respectively.

It should be understood that, after reading the present disclosure, other configurations of the engaging member switch 810 are contemplated as being within the scope of the present disclosure so long as its intended function is achieved. For example, in certain embodiments, the engaging member switch 810 is mounted on, e.g., attached to an outer surface of or embedded in, the engaging member 150 so as to be co-movable therewith and the switch actuator thereof is switched on and off when the engaging member 150 moves between the engaged and disengaged positions, respectively.

Figure 9:
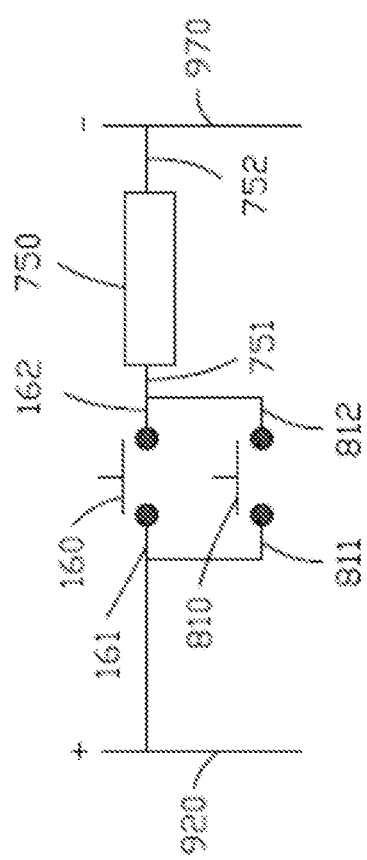
FIG. 9 is a schematic diagram illustrating an on/off switch and an engaging member switch of the surgical power drill system of FIG. 8 according to the second exemplary embodiment of the present disclosure.

FIG. 9 is a schematic diagram illustrating the on/off switch 160 and the engaging member switch 810 of the surgical power drill system 800 according to the second exemplary embodiment of the present disclosure. As illustrated in FIG. 9, the on/off switch 160 includes a first switch terminal 161 electrically connected to a positive terminal 920 of the surgical power drill system 800 and a second switch terminal 162 electrically connected to a first motor terminal 751 of the motor 750 of the surgical power drill system 800. The motor 750 further includes a second motor terminal 752 electrically connected to a negative terminal 970 of the surgical power drill system 800. The positive and negative terminals 920, 970 of the surgical power drill system 800 are configured to be connected to positive and negative terminals of a power source, e.g., battery, respectively.

The engaging member switch 810 is in parallel with the on/off switch 160. In particular, the engaging member switch 810 includes first and second switch terminals 811, 812 electrically and respectively connected to the first and second switch terminals 161, 162 of the on/off switch 160.

In operation, when it is desired to grind and drill a hole in an object, e.g., a bone of a patient, using the surgical power drill system 800 of the present disclosure, with further reference to FIG. 8, a shank of a tool bit 190, e.g., a burr screw, is fixed into the tool holder 120. Then, a tip of the tool bit 190 is aligned with and pressed against a marked location on the object. Next, the switch actuator of the on/off switch 160 is depressed, thereby turning the motor 750 on. At this time, the motor shaft 220 rotates, resulting in co-rotation of the tool holder 120 as well as the tool bit 190, thereby grinding the object. Thereafter, the switch actuator of the on/off switch 160 is switched off.

Next, the engaging member 150 is moved from the disengaged position, as shown in FIG. 5, to the engaged position, as shown in FIG. 6. This switches on the switch actuator of the engaging member switch 810 by the head member 270 of the engaging member 150, thereby switching the motor 750 on. This, in turn, rotates the motor shaft, e.g., motor shaft 220, resulting in co-rotation of the tool holder 120 as well as the tool bit 190. At this time, the driving unit, e.g., driving unit 200, moves from the distal position, as shown in, e.g., FIG. 2, to the proximate position, as shown in, e.g., FIG. 4, whereby a hole is drilled in the object.

From the above, when the engaging member 150 is moved to the engaged position, the switch actuator of the engaging member switch 810 is switched on by the engaging member 150. As such, drilling may be performed by simply moving the engaging member 150 to the engaged position, i.e., without the need to depress the switch actuator of the on/off switch 160, making operation of the surgical power drill system 800 of the present disclosure relatively easy.

Figure 10:
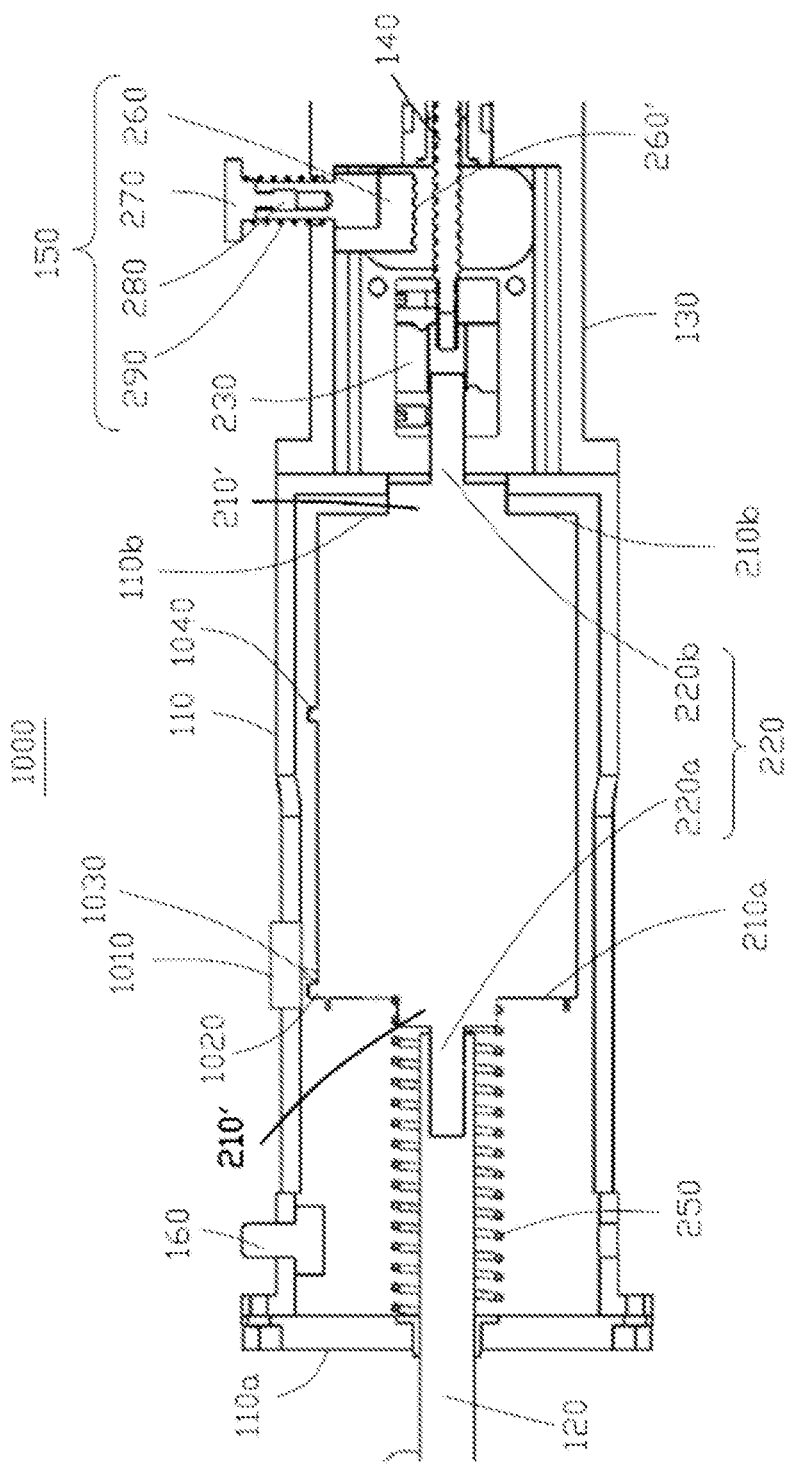
FIG. 10 is a partial schematic cross-sectional view illustrating a surgical power drill system according to the third exemplary embodiment of the present disclosure.
Figure 11:
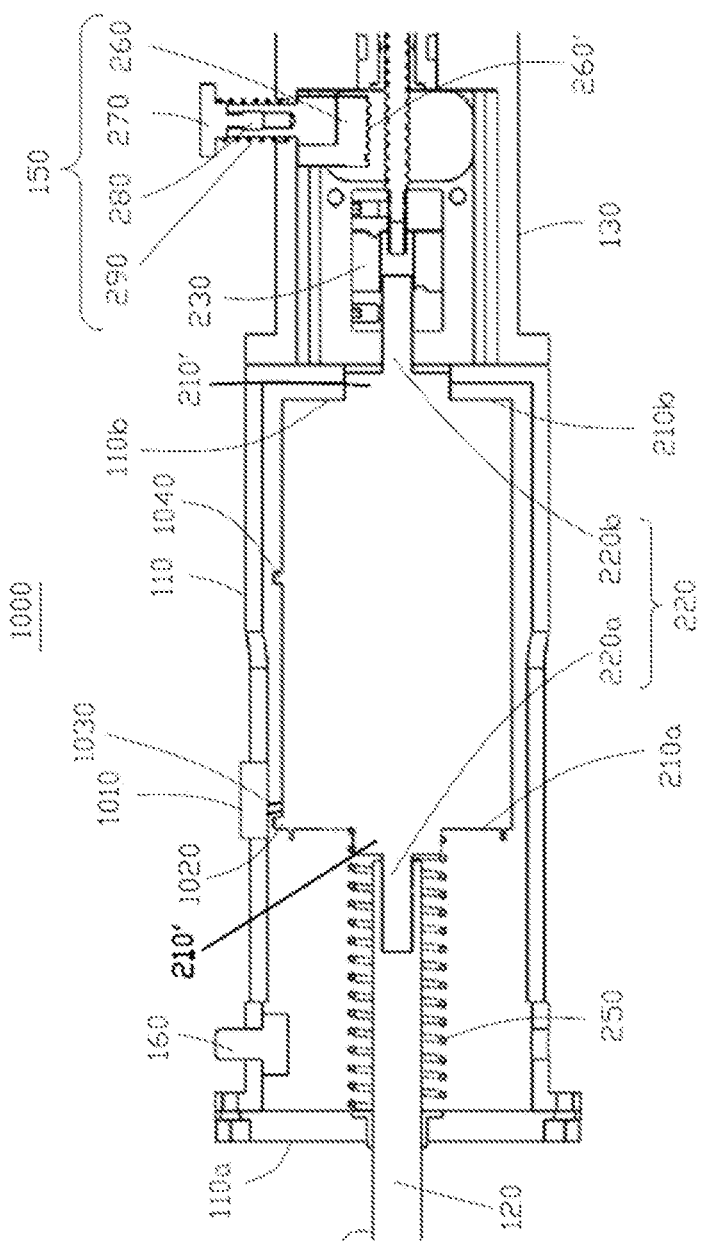
FIG. 11 is a schematic cross-sectional view illustrating a state where a driving unit of the surgical power drill system of FIG. 10 is at a distal position according to the third exemplary embodiment of the present disclosure.
Figure 12:
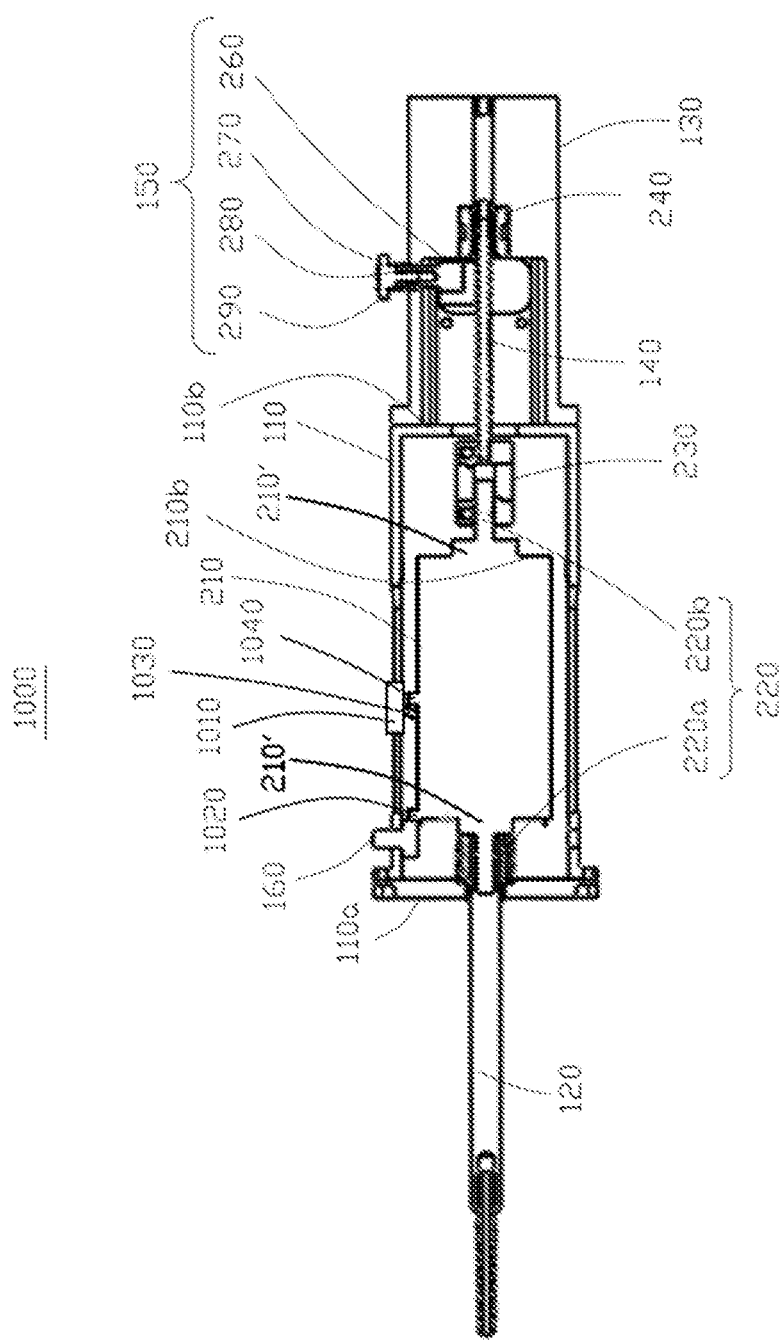
FIG. 12 is a schematic cross-sectional view illustrating a state where a driving unit of the surgical power drill system of FIG. 10 is beyond a proximate position according to the third exemplary embodiment of the present disclosure.

FIG. 10 is a partial schematic cross-sectional view illustrating a surgical power drill system 1000 according to the third exemplary embodiment of the present disclosure. FIG. 11 is a schematic cross-sectional view illustrating a state where the driving unit 200 of the surgical power drill system 1000 is at a distal position according to the third exemplary embodiment of the present disclosure. FIG. 12 is a schematic cross-sectional view illustrating a state where the driving unit 200 of the surgical power drill system 1000 is beyond the proximate position according to the third exemplary embodiment of the present disclosure. As illustrated in FIG. 10, the surgical power drill system 1000 differs from the surgical power drill system 100 in that the surgical power drill system 1000 further includes a driving unit switch 1010 mounted on the drill housing 110 and electrically connected to a motor, e.g., motor 750, of a driving unit, e.g., driving unit 200, of the surgical power drill system 1000. In this exemplary embodiment, the driving unit switch 1010 includes a switch actuator 1030 that extends into the drill housing 110. The biasing member 250 is configured to bias the driving unit 200 to an initial position between the distal and proximate positions.

A first protruding member 1020 protrudes from the motor casing 210, e.g., from a top surface of the motor casing 210, at the front end 210a of the motor casing 210. The first protruding member 1020 is configured to switch on the switch actuator 1030 of the driving unit switch 1010 when the driving unit 200 moves to the distal position, as illustrated in FIG. 11.

A second protruding member 1040 protrudes from the motor casing 210, e.g., from the top surface of the motor casing 210, between the front and rear ends 210*a*, 210*b* of the motor casing 210. The second protruding member 1040 is configured to switch off the switch actuator 1030 of the driving unit switch 1010 when the driving unit 200 moves beyond the proximate position, as illustrated in FIG. 12. In this exemplary embodiment, a distance between the first and second protruding members 1020, 1040 is, e.g., from about 30 mm to about 70 mm.

It should be understood that, after reading the present disclosure, other configurations of the driving unit switch 1010 are contemplated as being within the scope of the present disclosure so long as its intended function is achieved. For example, in some embodiments, the surgical power drill system 1000 includes a single protruding member that protrudes from the motor casing 210 and that is configured to switch on and off the driving unit switch 1010 when the driving unit 200 moves to the distal position and beyond the proximate position, respectively. In other embodiments, the surgical power drill system 1000 is dispensed with the first and second protruding members 1020, 1040. In such other embodiments, the driving unit switch 1010 is switched on by the rear end 210*b* of the motor casing 210 when the driving unit 200 moves to the distal position and is switched off by the front end 210*a* of the motor casing 210 when the driving unit 200 moves beyond the proximate position.

Figure 13:
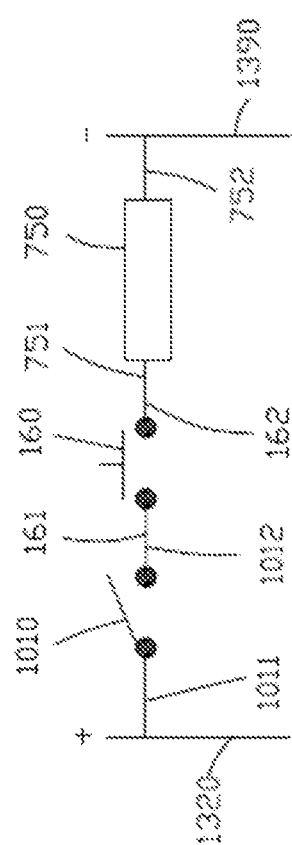
FIG. 13 is a schematic diagram illustrating an on/off switch and a driving unit switch of the surgical power drill system of FIG. 10 according to the third exemplary embodiment of the present disclosure.

FIG. 13 is a schematic diagram illustrating the on/off switch 160 and the driving unit switch 1010 of the surgical power drill system 1000 according to the third exemplary embodiment of the present disclosure. As illustrated in FIG. 13, the driving unit switch 1010 is in series with the on/off switch 160. In particular, the driving unit switch 1010 has a first switch terminal 1011 electrically connected to the positive terminal 1320 of the surgical power drill system 1000 and a second switch terminal 1012 electrically connected to a first switch terminal 161 of the on/off switch 160. The on/off switch 160 further includes a second switch terminal 162 electrically connected to a first motor terminal 751 of the motor 750. The motor 750 further includes a second motor terminal 752 electrically connected to a negative terminal 1390 of the surgical power drill system 1000. The positive and negative terminals 1320, 1390 of the surgical power drill system 1000 are configured to be connected to positive and negative terminals of a power source, e.g., battery, respectively.

In operation, when it is desired to grind or make a hole in an object, e.g., a bone of a patient, using the surgical power drill system 1000 of the present disclosure, with further reference to FIGS. 10-12, a shank of a tool bit 190, e.g., a burr screw, is fixed into the tool holder 120. Then, a tip of the tool bit 190 is aligned with and pressed against a marked location on the object. This moves the driving unit 200 from an initial position between the distal and proximate positions, as shown in FIG. 10, to the distal position, as shown in FIG. 11. This, in turn, switches on the switch actuator 1030 of the driving unit switch 1010 by the first protruding member 1020.

Next, the switch actuator of the on/off switch 160 is depressed, thereby turning the motor 750 on. At this time, the motor shaft 220 rotates, resulting in co-rotation of the tool holder 120, thereby grinding the object.

Next, the engaging member 150 is moved from the disengaged position, as shown in, e.g., FIG. 5, to the engaged position, as shown in, e.g., FIG. 6. This moves the driving unit 200 from the distal position, as shown in FIG. 11, to the proximate position, whereby a hole is drilled in the object.

Thereafter, when the driving unit 200 moves beyond the proximate position, as shown in FIG. 12, the second protruding member 1040 switches off the switch actuator 1030 of the driving unit switch 1010. At this time, the motor 750 is turned off, stopping the drilling procedure. The construction as such prevents the surgical power drill system 1000 of the present disclosure from making a hole in an undesired location of the object.

Figure 14:
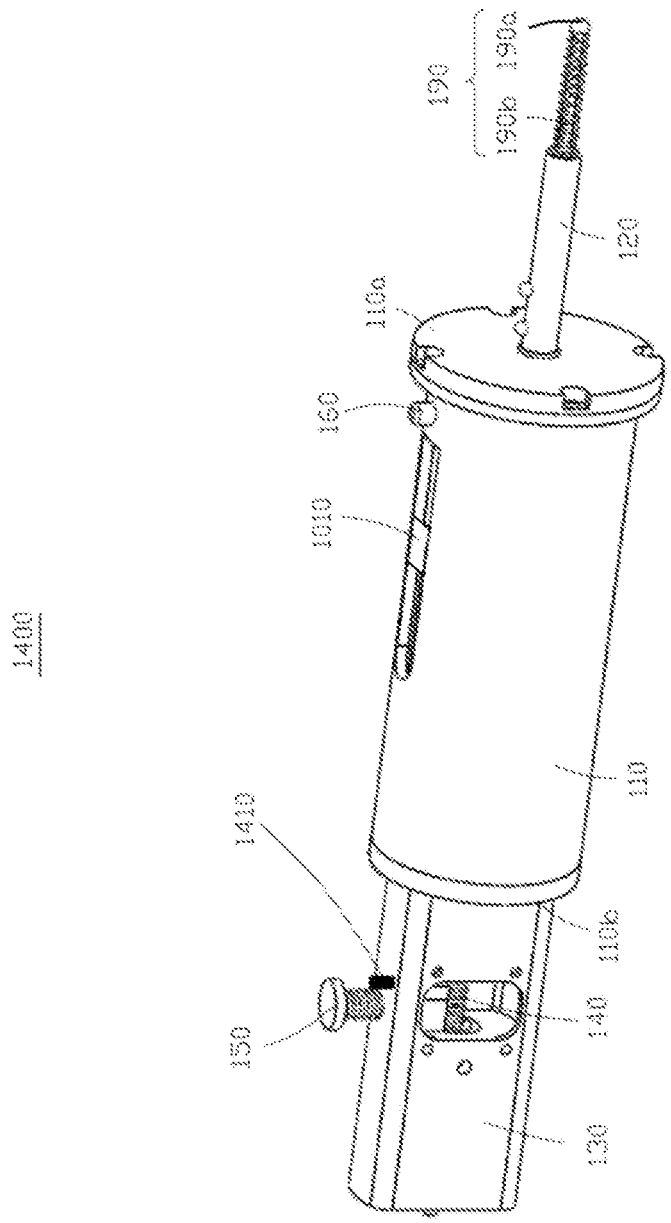
FIG. 14 is a schematic perspective view illustrating a surgical power drill system according to the fourth exemplary embodiment of the present disclosure.

FIG. 14 is a schematic perspective view illustrating a surgical power drill system 1400 according to the fourth exemplary embodiment of the present disclosure. As illustrated in FIG. 14, the surgical power drill system 1400 differs from the surgical power drill system 1000 in that the surgical power drill system 1400 further includes an engaging member switch 1410 mounted on the housing extension 130 and electrically connected to a motor, e.g., motor 750 of a driving unit, e.g., driving unit 200, of the surgical power drill system 1400. In this exemplary embodiment, the engaging member switch 1410 includes a switch actuator that protrudes from the housing extension 130, e.g., from a top surface of the housing extension 130, and that is arranged adjacent a neck member, e.g., neck member 280, under a head member, e.g., head member 270. The construction as such permits the engaging member 150 to switch the engaging member switch 1410 on and off when the engaging member 150 moves between the engaged and disengaged positions, respectively.

It should be understood that, after reading the present disclosure, other configurations of the engaging member switch 1410 are contemplated as being within the scope of the present disclosure so long as its intended function is achieved. For example, in certain embodiments, the engaging member switch 1410 is mounted on, e.g., attached to an outer surface of or embedded in, the engaging member 150 so as to be co-movable therewith and the switch actuator thereof is switched on and off when the engaging member 150 moves between the engaged and disengaged positions, respectively.

Figure 15:
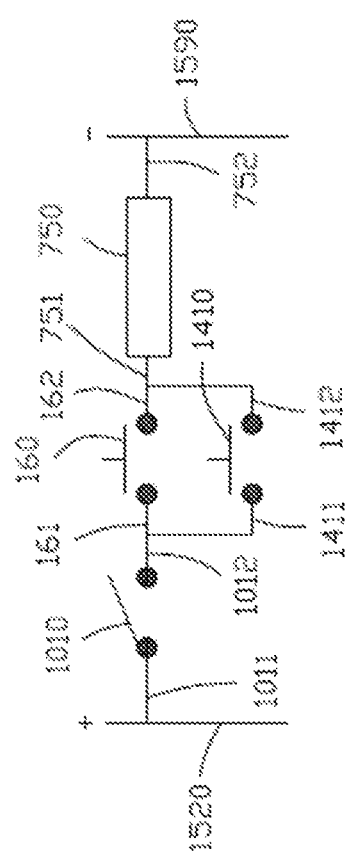
FIG. 15 is a schematic diagram illustrating an on/off switch, a driving unit switch, and an engaging member switch of the surgical power drill system of FIG. 14 according to the fourth exemplary embodiment of the present disclosure.

FIG. 15 is a schematic diagram illustrating the on/off switch 160, the driving unit switch 1010, and the engaging member switch 1410 of the surgical power drill system 1400 according to the fourth exemplary embodiment of the present disclosure. As illustrated in FIG. 15, the driving unit switch 1010 is in series with the on/off switch 160. In particular, the driving unit switch 1010 has a first switch terminal 1011 electrically connected to a positive terminal 1520 of the surgical power drill system 1400 and a second switch terminal 1012 electrically connected to a first switch terminal 161 of the on/off switch 160. The on/off switch 160 further includes a second switch terminal 162 electrically connected to a first motor terminal 751 of the motor 750. The motor 750 further includes a second motor terminal 752 electrically connected to a negative terminal 1590 of the surgical power drill system 1400. The positive and negative terminals 1520, 1590 of the surgical power drill system 1400 are configured to be connected to positive and negative terminals of a power source, e.g., battery, respectively.

The engaging member switch 1410 is in parallel with the on/off switch 160. In particular, the engaging member switch 1410 includes first and second switch terminals 1411, 1412 electrically and respectively connected to the first and second switch terminals 161, 162 of the on/off switch 160.

In operation, when it is desired to grind or make a hole in an object, e.g., a bone of a patient, using the surgical power drill system 1400 of the present disclosure, with further reference to FIG. 14, a shank of a tool bit 190, e.g., a burr screw, is fixed into the tool holder 120. Then, a tip of the tool bit 190 is aligned with and pressed against a marked location on the object. This moves the driving unit 200 from an initial position between the distal and proximate positions, as shown in, e.g., FIG. 10, to the distal position, as shown in, e.g., FIG. 11. This, in turn, switches on the switch actuator 1030 of the driving unit switch 1010 by the first protruding member 1020.

Next, the switch actuator of the on/off switch 160 is depressed, thereby turning the motor 750 on. At this time, the motor shaft, e.g., motor shaft 220, rotates, resulting in co-rotation of the tool holder 120 as well as the tool bit 190, thereby grinding the object. Thereafter, the switch actuator of the on/off switch 160 is switched off.

Next, the engaging member 150 is moved from the disengaged position, as shown in, e.g., FIG. 5, to the engaged position, as shown in, e.g., in FIG. 6. This switches on the switch actuator of the engaging member switch 1410 by the head member 270 of the engaging member 150, thereby turning the motor 750 on. This, in turn, rotates the motor shaft, e.g., motor shaft 220, resulting in co-rotation of the tool holder 120. At this time, the driving unit 200 moves from the distal position, as shown in, e.g., FIG. 11, to the proximate position, whereby a hole is drilled in the object.

Thereafter, when the driving unit 200 moves beyond the proximate position, as shown in, e.g., FIG. 12, the second protruding member, e.g., second protruding member 1040, switches off the switch actuator, e.g., switch actuator 1030, of the driving unit switch 1010. At this time, the motor 750 is turned off, stopping the drilling procedure. The construction as such prevents the surgical power drill system 1400 of the present disclosure from making a hole in an undesired location of the object.

From the above, when the engaging member 150 is moved to the engaged position, the switch actuator of the engaging member switch 1410 is switched on by the engaging member 150. As such, drilling may be performed by simply moving the engaging member 150 to the engaged position, i.e., without the need to depress the switch actuator of the on/off switch 160, making operation of the surgical power drill system 1400 of the present disclosure relatively easy.

Although the surgical power drill systems 800, 1000, 1400 are exemplified with switches 810, 1010, 1410 that have switch actuators, e.g., switch actuator 1030, other configurations of the switches 810, 1010, 1410 are contemplated as being within the scope of the present disclosure so long as their intended functions are achieved. For example, in certain embodiments, at least one of the switches 810, 1010, 1410 may include a motion sensor, e.g., infrared, acoustic, magnetic, and the like, that detects a motion or change in the position of the engaging member 150/driving unit 200.

Figure 16:
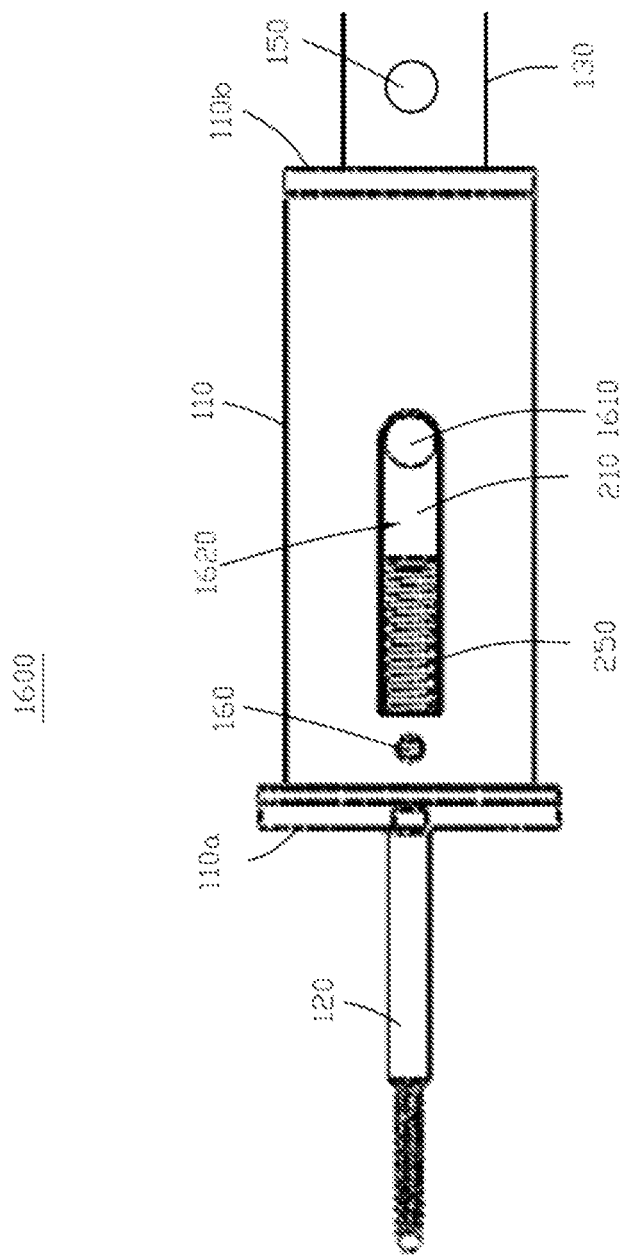
FIG. 16 is a schematic top view illustrating a surgical power drill system according to the fifth exemplary embodiment of the present disclosure.

FIG. 16 is a schematic top view illustrating a surgical power drill system 1600 according to the fifth exemplary embodiment of the present disclosure. As illustrated in FIG. 16, this embodiment differs from the previous embodiments in that the surgical power drill system 1600 further includes a marker 1610 arranged on the motor casing 210 so as to be co-movable therewith and is exposed through a window 1620 in the drill housing 110, thereby allowing tracking of positions of the motor casing 210 by a computer system via a spatial sensor, e.g., camera.

In certain embodiments, at least one of the motor casing 210, the tool holder 120, and the screw member 140 is provided with a marker, e.g., marker 1610.

In some embodiments, the marker 1610 is an active marker. In such some embodiments, the signal emitted by the marker 1610 is generated by the marker 1610 itself. For example, the marker 1610 is configured to emit an electromagnetic signal, a sound wave, a heat, any perceivable signal, or a combination thereof. In other embodiments, the marker 1610 is a passive marker. In such other embodiments, the marker 1610 is covered with a reflective material and the signal emitted by the marker 1610 is a signal reflected thereby.

In certain embodiments, the marker 1610 is an active and passive marker. In such certain embodiments, the marker 1610 is configured to generate a signal and is covered with a reflective material.

Figure 17:
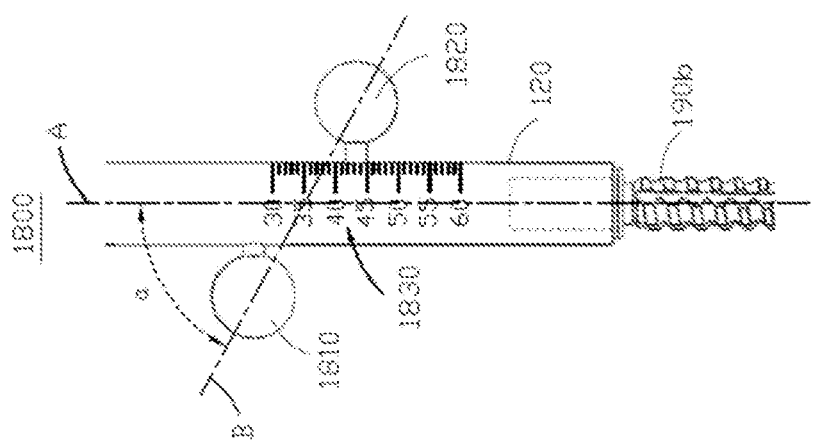
FIG. 17 is a partial schematic top view illustrating a surgical power drill system according to the sixth exemplary embodiment of the present disclosure.

FIG. 17 is a partial schematic top view illustrating a surgical power drill system 1700 according to the sixth exemplary embodiment of the present disclosure. As illustrated in FIG. 17, the surgical power drill system 1700 differs from the surgical power drill system 1600 in that the surgical power drill system 1700 further includes a pair of markers 1710, 1720 configured to absorb a radiation, such as an X-ray. Examples of materials for the markers 1710, 1720 include, but are not limited to, metals and ceramics. In this exemplary embodiment, the markers 1710, 1720 are arranged on the tool holder 120 of the surgical power drill system 1700 along the shaft axis (A) of the surgical power drill system 1700, thereby allowing tracking of positions of the tool holder 120 by, e.g., an X-ray imaging system.

In some embodiments, at least one of the markers 1710, 1720 is an active marker. In such some embodiments, the signal emitted by the at least one of the markers 1710, 1720 is generated by the at least one of the markers 1710, 1720 itself. For example, one or both of the markers 1710, 1720 are configured to emit an electromagnetic signal, a sound wave, a heat, any perceivable signal, or a combination thereof. In other embodiments, at least one of the markers 1710, 1720 is a passive marker. In such other embodiments, the at least one of the markers 1710, 1720 is covered with a reflective material and the signal emitted by the at least one of the markers 1710, 1720 is a signal reflected thereby.

In certain embodiments, at least one of the markers 1710, 1720 is an active and passive marker. In such certain embodiments, the at least one of the markers 1710, 1720 is configured to generate a signal and is covered with a reflective material.

Figure 18:
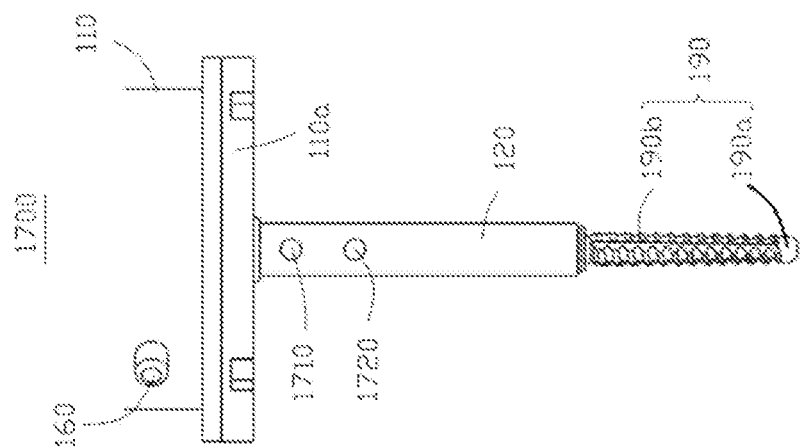
FIG. 18 is a partial schematic top view illustrating a surgical power drill system according to the seventh exemplary embodiment of the present disclosure.

FIG. 18 is a partial schematic top view illustrating a surgical power drill system 1800 according to the seventh exemplary embodiment of the present disclosure. As illustrated in FIG. 18, the surgical power drill system 1800 differs from the surgical power drill system 1600 in that the surgical power drill system 1800 further includes a pair of markers 1810, 1820 configured to absorb a radiation, such as an X-ray. Examples of materials for the markers 1810, 1820 include, but are not limited to, metals and ceramics. In this exemplary embodiment, the markers 1810, 1820 are arranged on opposite sides of the tool holder 120, respectively. At least one of the markers 1810, 1820 is movable along the length of the tool holder 120. For example, in some embodiments, one of the markers 1810, 1820 is fixedly mounted on the tool holder 120 and the other of the markers 1810, 1820 is movable along the length of the tool holder 120. In other embodiments, both the markers 1810, 1820 are movable along the length of the tool holder 120.

The surgical power drill system 1800 further includes a set of angle indicia 1830 that is arranged on the tool holder 120 and that measures an angle (a) between the shaft axis (A) and a line (B) that intersects the markers 1810, 1820.

In use, one or both of the markers 1810, 1820 are adjusted with reference to the angle indicia 1830 such that a marker angle is formed therebetween. Next, the surgical power drill system 1800 is brought in contact with an object, e.g., a bone of a patient, such that a contact angle is formed therebetween. Thereafter, an image, e.g., an X-ray image, of the surgical power drill system 1800 and the object is taken to confirm whether the contact angle corresponds to the marker angle.

In some embodiments, at least one of the markers 1810, 1820 is an active marker. In such some embodiments, the signal emitted by the at least one of the markers 1810, 1820 is generated by the at least one of the markers 1810, 1820 itself. For example, one or both of the markers 1810, 1820 is configured to emit an electromagnetic signal, a sound wave, a heat, any perceivable signal, or a combination thereof. In other embodiments, at least one of the markers 1810, 1820 is a passive marker. In such other embodiments, the at least one of the markers 1810, 1820 is covered with a reflective material and the signal emitted by the at least one of the markers 1810, 1820 is a signal reflected thereby.

In certain embodiments, at least one of the markers 1810, 1820 is an active and passive marker. In such certain embodiments, the at least one of the markers 1810, 1820 is configured to generate a signal and is covered with a reflective material.

Figure 19:
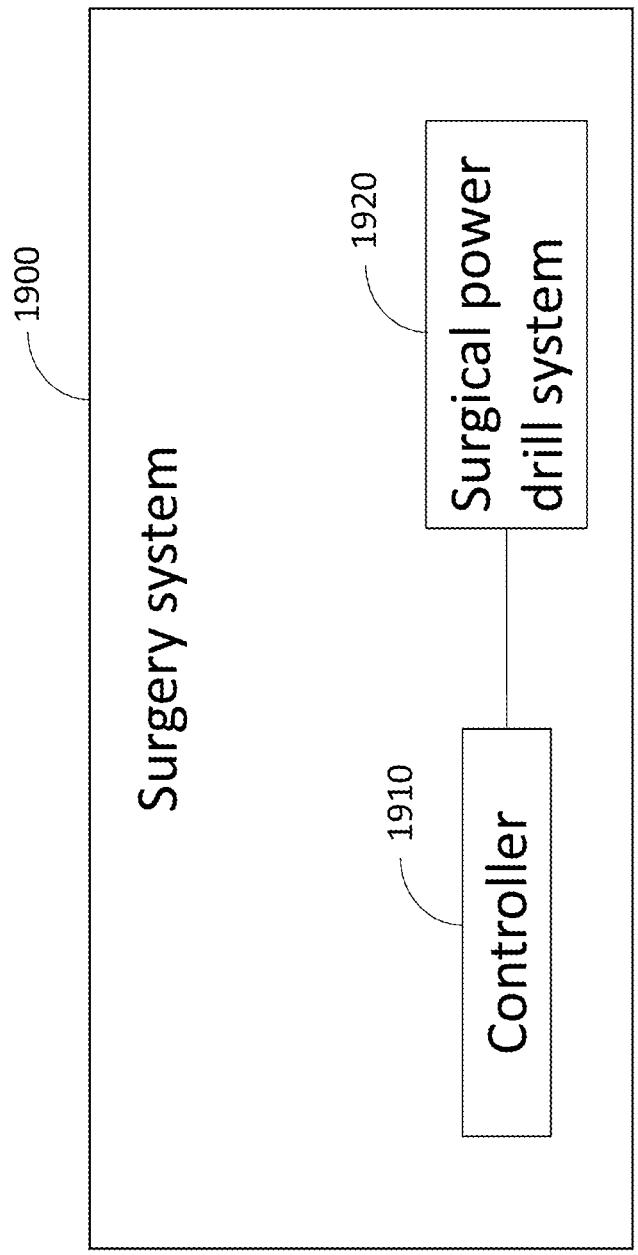
FIG. 19 is a schematic block diagram illustrating a surgery system according to an exemplary embodiment of the present disclosure.

In certain embodiments, an instrument, e.g., a robotic arm, may be used to control movements and operations of the surgical power drill system 100, 800, 1000, 1400, 1600, 1700, 1800, 1700, or 1800. For example, FIG. 19 is a schematic block diagram illustrating a surgery system 1900 according to an exemplary embodiment of the present disclosure. As illustrated in FIG. 19, the surgery system 1900, e.g., an orthopedic surgery system, includes a controller 1910 and a surgical power drill system 1920. The surgical power drill system 1920 may be one of the surgical power drill systems 100, 800, 1000, 1400, 1600, 1700, 1800. The controller 1910 is connected to and configured to control movements and operations of the surgical power drill system 1920.

In an embodiment, a surgical power drill system comprises a housing unit, a driving unit, a tool holder, and a screw member. The driving unit is movably mounted in the housing unit and includes a motor and a motor shaft coupled to the motor. The driving unit is movable relative to the housing unit between a distal position, where the driving unit is distal from a front end of the housing unit, and a proximate position, where the driving unit is proximate to the front end of the housing unit. The tool holder is coupled to a first end portion of the motor shaft. The screw member is coupled to a second end portion of the motor shaft.

In another embodiment, a surgical power drill system comprises a housing unit, a driving unit, a tool holder, and a driving unit switch. The driving unit is movably mounted in the housing unit and includes a motor and a motor shaft coupled to the motor. The tool holder is coupled to a first end portion of the motor shaft. The driving unit switch is coupled to the motor and is configured to be switched on and off by the driving unit.

In another embodiment, a surgical power drill system comprises a housing unit, a driving unit, a tool holder, and an engaging member. The driving unit is movably mounted in the housing unit and includes a motor and a motor shaft coupled to the motor. The driving unit is movable relative to the housing unit between a distal position, where the driving unit is distal from a front end of the housing unit, and a proximate position, where the driving unit is proximate to the front end of the housing unit. The tool holder is coupled to a first end portion of the motor shaft. The engaging member extends into the housing unit and is configured to engage the motor shaft to move the driving unit to the proximate position.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A surgical power drill system comprising:
   a housing unit;
   a driving unit movably mounted in the housing unit and including:
      a motor, and
      a motor shaft coupled to the motor, wherein the driving unit is movable relative to the housing unit between a distal position, where the driving unit is distal from a front end of the housing unit, and a proximate position, where the driving unit is proximate to the front end of the housing unit;
   a tool holder coupled to a first end portion of the motor shaft; and
   a screw member coupled to a second end portion of the motor shaft;
   wherein, when the motor is turned on, the tool holder, the first and second end portions of the motor shaft, and the screw member rotate simultaneously.

2. The surgical power drill system of claim 1, wherein the motor shaft is rotatable about a shaft axis and each of the tool holder and the screw member extends along the shaft axis.

3. The surgical power drill system of claim 1, wherein the motor shaft, the tool holder, and the screw member are tubular and in fluid communication with each other.

4. The surgical power drill system of claim 1, further comprising an engaging member movably mounted on the housing unit and formed with a thread, wherein the engaging member is movable relative to the housing unit so as to engage or disengage the screw member.

5. The surgical power drill system of claim 4, wherein the engaging member includes:
   a body member formed with the thread,
   a head member,
   a neck member that extends through the housing unit and that is between the body member and the head member; and
   a biasing member sleeved on the neck member and configured to bias the engaging member to disengage the screw member.

6. The surgical power drill system of claim 4, further comprising an engaging member switch coupled to the motor and configured to be switched on and off by the engaging member.

7. The surgical power drill system of claim 6, further comprising an on/off switch coupled to the motor and in parallel with the engaging member switch.

8. The surgical power drill system of claim 1, further comprising a driving unit switch coupled to the motor and configured to be switched on and off by the driving unit.

9. The surgical power drill system of claim 8, further comprising a first protruding member formed on the driving unit and configured to switch the driving unit switch on when the driving unit moves to the distal position.

10. The surgical power drill system of claim 9, further comprising a second protruding member formed on the driving unit and configured to switch the driving unit switch off when the driving unit moves beyond the proximate position.

11. A surgical power drill system comprising:
a housing unit;
a driving unit movably mounted in the housing unit and including:
a motor, and
a motor shaft coupled to the motor and, wherein the driving unit is movable relative to the housing unit between a distal position, where the driving unit is distal from a front end of the housing unit, and a proximate position, where the driving unit is proximate to the front end of the housing unit;
a tool holder coupled to a first end portion of the motor shaft;
an engaging member extending into the housing unit and configured to engage the motor shaft to move the driving unit from the distal position to the proximate position; and
a screw member coupled to a second end portion of the motor shaft;
wherein, when the motor is turned on, the tool holder, the first and second end portions of the motor shaft, and the screw member rotate simultaneously.

12. The surgical power drill system of claim 11, wherein the housing unit includes a drill housing and a housing extension coupled to a rear end of the drill housing, the driving unit is in the drill housing, and the engaging member is mounted on the housing extension.

13. The surgical power drill system of claim 11, further comprising a biasing member configured to bias the driving unit to the distal position.

14. The surgical power drill system of claim 11, wherein the housing unit is magnetic.

15. The surgical power drill system of claim 11, further comprising a marker configured to emit a signal and arranged on the driving unit so as to be co-movable therewith.

16. The surgical power drill system of claim 11, further comprising:
a first marker configured to absorb a radiation and mounted on the tool holder;
a second marker configured to absorb a radiation and mounted on the tool holder; and
a set of angle indicia on the tool holder.

17. The surgical power drill system of claim 11, further comprising one or more markers mounted on at least one of the driving unit, the motor shaft, and the tool holder.

* * * * *